(12) United States Patent
Abe et al.

(10) Patent No.: US 10,592,740 B2
(45) Date of Patent: Mar. 17, 2020

(54) CONTROL SYSTEM, INFORMATION PROCESSING DEVICE, CONTROL METHOD, AND PROGRAM

(71) Applicant: SONY CORPORATION, Tokyo (JP)

(72) Inventors: Takashi Abe, Tokyo (JP); Takeo Tsukamoto, Tokyo (JP); Shuichi Konami, Chiba (JP); Tomoyuki Ito, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/519,568

(22) PCT Filed: Aug. 18, 2015

(86) PCT No.: PCT/JP2015/073088
§ 371 (c)(1),
(2) Date: Apr. 17, 2017

(87) PCT Pub. No.: WO2016/080031
PCT Pub. Date: May 26, 2016

(65) Prior Publication Data
US 2017/0255823 A1 Sep. 7, 2017

(30) Foreign Application Priority Data

Nov. 20, 2014 (JP) .................. 2014-235486

(51) Int. Cl.
*G06K 9/00* (2006.01)
*A61B 5/117* (2016.01)
(Continued)

(52) U.S. Cl.
CPC ........ *G06K 9/00617* (2013.01); *A61B 3/0008* (2013.01); *A61B 3/10* (2013.01);
(Continued)

(58) Field of Classification Search
None
See application file for complete search history.

(56) References Cited

U.S. PATENT DOCUMENTS

| 4,641,349 A | 2/1987 | Flom et al. |
| 7,076,087 B2 * | 7/2006 | Wakiyama ......... G06K 9/00597 382/117 |

(Continued)

FOREIGN PATENT DOCUMENTS

JP 2013-518319 A 5/2013

OTHER PUBLICATIONS

International Search Report dated Oct. 6, 2015 in PCT/JP2015/073088.

*Primary Examiner* — Soo Jin Park
(74) *Attorney, Agent, or Firm* — Xsensus, LLP (57) ABSTRACT

[Object] To provide a control system, an information processing device, a control method, and a program capable of capturing a clear iris image having no reflected light of illumination without interfering with a user's field of view. [Solution] A control system including: an illumination section configured to irradiate any one of left and right eyes with light; an imaging section configured to image the other eye different from the one of the left and right eyes; and a control section configured to perform control to cause the imaging section to image the other eye while the illumination section is irradiating the one of the left and right eyes with light.

14 Claims, 7 Drawing Sheets

(51) Int. Cl.
  *G06T 1/00*    (2006.01)
  *G06T 7/00*    (2017.01)
  *A61B 5/107*   (2006.01)
  *A61B 3/10*    (2006.01)
  *A61B 3/00*    (2006.01)
  *A61B 5/00*    (2006.01)
  *A61B 3/11*    (2006.01)

(52) U.S. Cl.
  CPC ............ *A61B 3/112* (2013.01); *A61B 5/1075* (2013.01); *A61B 5/1079* (2013.01); *A61B 5/117* (2013.01); *A61B 5/6803* (2013.01); *G06K 9/00604* (2013.01); *G06T 1/00* (2013.01); *G06T 7/00* (2013.01)

(56) References Cited

U.S. PATENT DOCUMENTS

| | | | |
|---|---|---|---|
| 2003/0058492 A1* | 3/2003 | Wakiyama | G06K 9/00597 359/20 |
| 2011/0033090 A1* | 2/2011 | Baughman | G06F 21/32 382/117 |
| 2013/0063582 A1 | 3/2013 | Choi et al. | |
| 2015/0234206 A1* | 8/2015 | Lee | G02C 7/085 351/206 |
| 2015/0294464 A1* | 10/2015 | Kim | G06K 9/00597 382/117 |

* cited by examiner

CONTROL SYSTEM, INFORMATION PROCESSING DEVICE, CONTROL METHOD, AND PROGRAM

TECHNICAL FIELD

The present disclosure relates to a control system, an information processing device, a control method, and a program.

BACKGROUND ART

There has been traditionally proposed a biometrics authentication technology that identifies individuals on the basis of human physical features. For examples, fingerprints, hand geometry, retinas, faces, voices, and the like are used for biometrics authentication. Further, the irises of the human eyeballs have different characteristics depending on individuals. For example, Patent Literature 1 below therefore proposes an iris authentication system that uses the features of the irises.

The irises of all the human eyes have immensely complicated unique tissues, and it is known that the tissues are essentially invariable. The tissues or details of both irises of even the same person are not the same. The iris dilates and constricts to adjust the dimension of the pupil in response to light. The iris pattern slightly varies at this time, and this variation affects the accuracy of authentication in some cases. Further, Patent Literature 2 below discloses a method of generating an iris code for a method of analyzing such features of the iris. Specifically, an iris in a captured image is recognized, the inner border of the iris (circular border between the iris and the pupil) and the outer border of the iris are decided, and the circular iris is separated. A polar coordinate system is then set on the separated iris image. The origin of the coordinate system is placed at the center of the circular border between the iris and the pupil. Afterwards, the feature value of the iris image subjected to the polar coordinate conversion is extracted, and an iris code having a fixed length and a universal format for all irises is generated. The iris code generated in this way is stored as a reference code. At the time of authentication, an iris code similarly encoded is compared with the reference code stored in advance, and it is determined whether the iris code and the reference code originate from the same individual.

Further, using a pupil having the same size as that of the registered pupil at the time of iris authentication improves the authentication accuracy. Accordingly, Patent Literature 3 below proposes a system that varies the pupil of an eye in size by gently varying the intensity of illumination over time, and continuously captures eye images in which the pupil is different in size.

Further, in a case where an iris is imaged by adjusting the size of the pupil, the eye is illuminated for the adjustment as a general method. The illumination light is reflected by the cornea in front of the iris at this time, and overlaps with the iris image as a bright spot in some cases. If the bright spot appears in the image to hide part of the iris pattern, the authentication accuracy is adversely affected very much. It is then necessary to capture an image while preventing the reflected light of the illumination from hiding the iris. For example, Patent Literature 4 below has the imaging direction agree with the optical axis of the illumination, thereby preventing a bright spot from hiding the iris.

CITATION LIST

Patent Literature

Patent Literature 1: JP 5-84166B
Patent Literature 2: JP 3307936B
Patent Literature 3: JP 2000-194855A
Patent Literature 4: JP 4527088B

DISCLOSURE OF INVENTION

Technical Problem

The method described in Patent Literature 4 above, however, requires a camera to be disposed right in front of an eye, which problematically interferes with the field of view.

The present disclosure then proposes a control system, an information processing device, a control method, and a program capable of capturing a clear iris image having no reflected light of illumination without interfering with a user's field of view.

Solution to Problem

According to the present disclosure, there is proposed a control system including: an illumination section configured to irradiate any one of left and right eyes with light; an imaging section configured to image the other eye different from the one of the left and right eyes; and a control section configured to perform control to cause the imaging section to image the other eye while the illumination section is irradiating the one of the left and right eyes with light.

According to the present disclosure, there is proposed an information processing device including: an imaging section configured to image any one of left and right eyes; an illumination section configured to irradiate the other eye different from the one of the left and right eyes with light; and a control section configured to perform control to cause the imaging section to image the one of the left and right eyes while the illumination section is irradiating the other eye with light.

According to the present disclosure, there is proposed a control method including: performing control to cause, while an illumination section is irradiating any one of left and right eyes with light, an imaging section to image the other eye different from the one of the left and right eyes.

According to the present disclosure, there is proposed a program for causing a computer to function as: a control section configured to perform control to cause, while an illumination section is irradiating any one of left and right eyes with light, an imaging section to image the other eye different from the one of the left and right eyes.

Advantageous Effects of Invention

As described above, according to the present disclosure, it is possible to capture a clear iris image having no reflected light of illumination without interfering with a user's field of view.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be made in the following order.
1. Overview of Information Processing System according to Embodiment of the Present Disclosure
2. Configuration
3. Operation processing
3-1. Registration Process
3-2. Authentication Process
4. Supplemental Information
5. Conclusion

Figure 1:
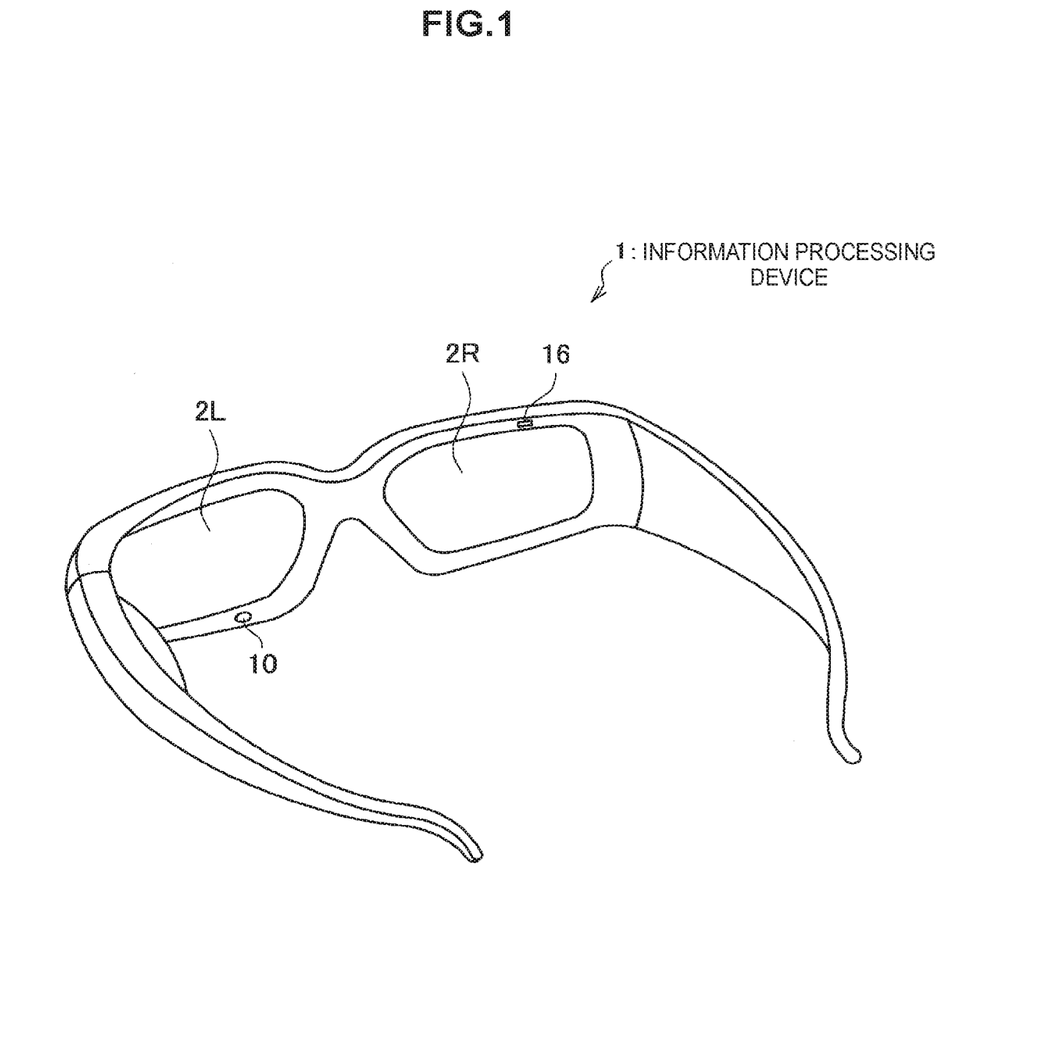
FIG. 1 is a diagram that describes an overview of an information processing system according to an embodiment of the present disclosure.

1. Overview of Information Processing System According to Embodiment of the Present Disclosure First of all, the overview of an information processing system according to an embodiment of the present disclosure will be illustrated in FIG. 1 and described. As illustrated in FIG. 1, the information processing system according to the present embodiment may be, for example, an information processing device 1 that is realized by a glasses-type wearable device (SmartEyeglass).

As illustrated in FIG. 1, the information processing device 1 includes a right-eye lens section 2R and a left-eye lens section 2L which are respectively positioned in front of the right eye of a user and the left eye of the user when the information processing device 1 is worn by the user. Further, the edge of the right-eye lens section 2R is provided with an illumination section 16 that irradiates the right eye with light, while the edge of the left-eye lens section 2L is provided with an imaging section 10 that images the left eye. Additionally, the positions for installing the illumination section 16 and the imaging section 10 are not limited to the example illustrated in FIG. 1. The illumination section 16 only has to be provided to irradiate any one of the left and right eyes with light. Further, the imaging section 10 only has to be provided to image the other eye different from the eye illuminated by the illumination section 16.

(Background)

In a case where the size of a pupil is adjusted, and then the iris is imaged at the time of iris authentication or registration, the eye is traditionally illuminated and the size of the pupil is adjusted as a general method. This is because the pupil respectively constricts and dilates as a physiological response when illuminated with increased light and decreased light.

Figure 2:
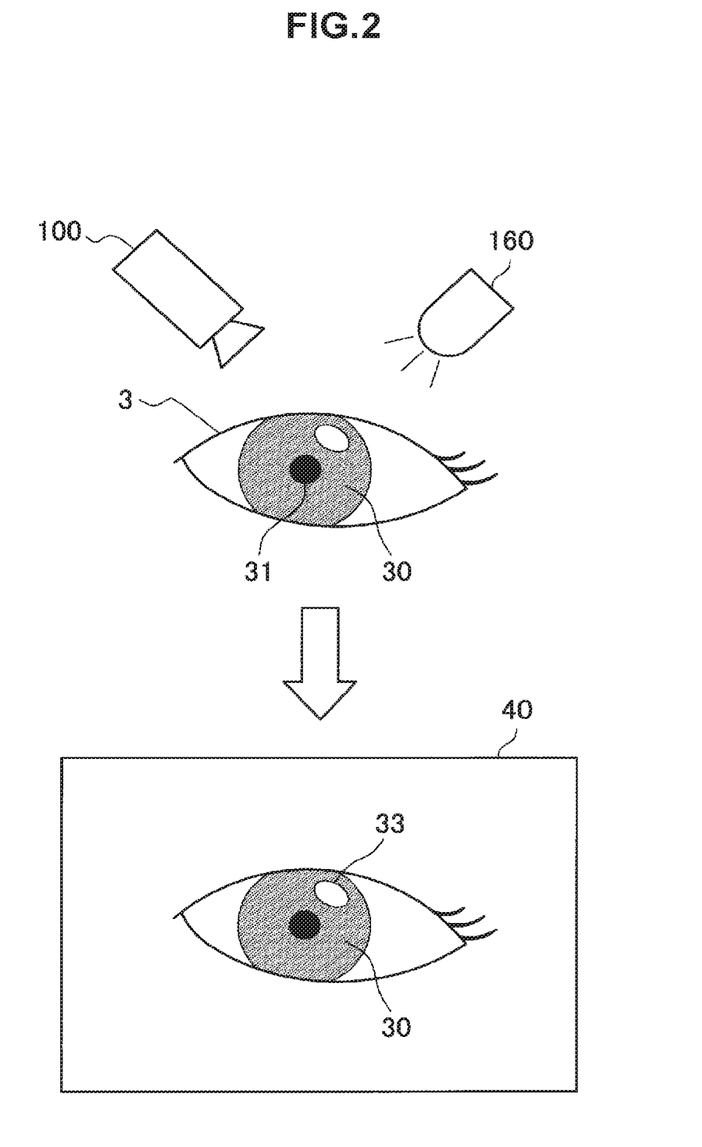
FIG. 2 is a diagram that describes a captured image of an iris imaged by a traditional technique.

However, if the iris is imaged while illuminated, the illumination light reflected by the cornea in front of the iris and serves as a bright spot to overlap with the iris image in some cases. If the bright spot appears in the iris image to hide part of the iris pattern, the authentication accuracy is adversely affected very much. FIG. 2 is a diagram that describes a captured image of an iris imaged by a traditional technique. As illustrated in FIG. 2, an illumination section 160 traditionally illuminates an eye 3 with light to adjust the size of a pupil 31, and an imaging section 100 images the eye 3. In this case, there is the problem as illustrated as a captured image 40 that the light from the illumination is reflected by the cornea in front of the iris 30 and appears in the image as a bright spot 33. If the bright spot 33 overlies the iris 30, part of the feature information of the iris 30 lacks. This adversely affects the authentication rate of iris authentication very much.

There is then proposed, in the present embodiment, a system that uses the consensual light reflex, and images, while illuminating one of the eyes to adjust the size of the pupil, the other eye not illuminated, thereby acquiring a clear iris image without being affected by the reflected light of the illumination. Once light is incident on the retina, this stimulus reaches the pretectal nucleus through the optic nerve, and relayed by the Edinger-Westphal (E-W) nucleus via the interneuron to the parasympathetic fiber of the oculomotor nerve. Further, the left and right pretectal nuclei are connected to each other via the posterior commissure. Accordingly, signals from one of the optic nerves are transmitted to both pretectal nuclei, and the pupils of both eyes constrict even in a case where only one of the eyes is illuminated with light. This constriction of a pupil that is not illuminated with light is generally referred to as consensual light reflex.

Figure 3:
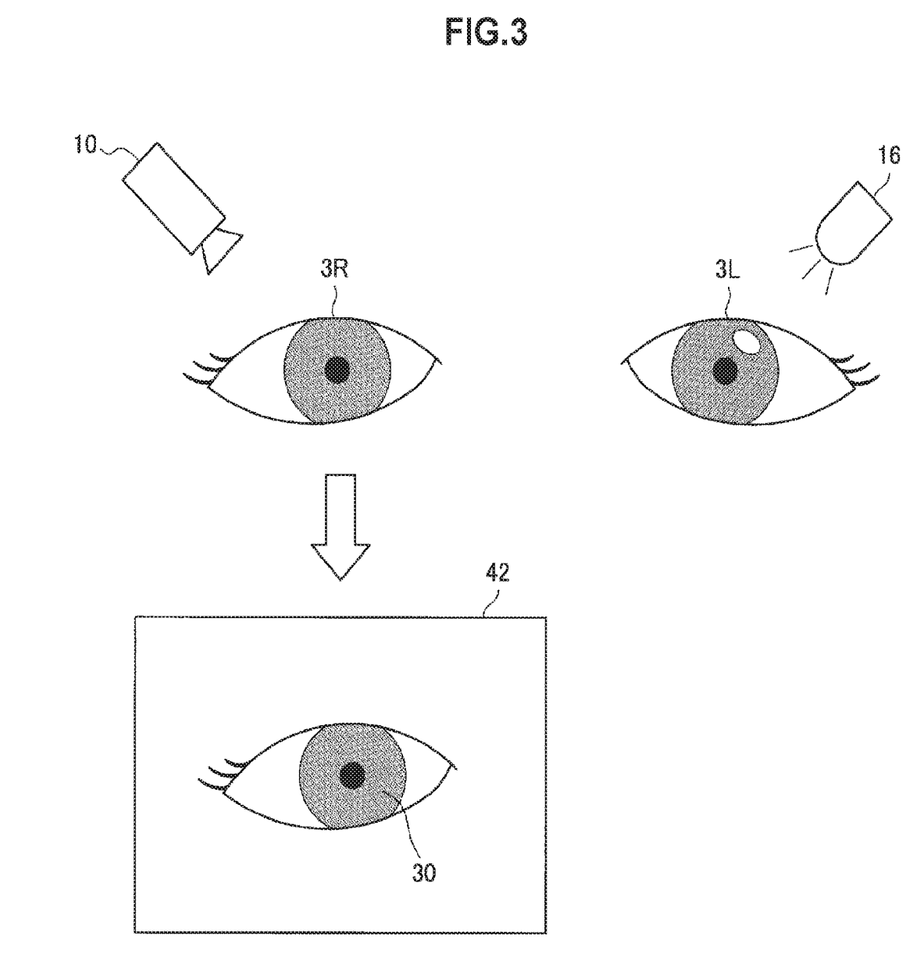
FIG. 3 is a diagram that describes a captured image of an iris imaged by a technique according to the present embodiment.

The above-described consensual light reflex is used in the present embodiment to acquire an iris image having no bright spot, for example, as illustrated in FIG. 3. FIG. 3 is a diagram that describes a captured image of an iris imaged by a technique according to the present embodiment. As illustrated in FIG. 3, once one of the eyes, for example, a left eye 3L is illuminated to adjust the size of the pupil, the pupil of an opposite right eye 3R also varies similarly in size because of the consensual light reflex in the present embodiment. Accordingly, the imaging section 100 images the right eye 3R. Imaging the eye that is not illuminated makes it possible to acquire a clear image of the iris 30 without being affected by the reflected light of the illumination as illustrated as a captured image 42.

The overview of the information processing system according to an embodiment of the present disclosure has been described above. Although FIG. 1 illustrates that the information processing device 1 is realized by a glasses-type wearable device (SmartEyeglass), the present disclosure is not limited thereto. The information processing device 1 may also be realized by a pair of goggles, a pair of binoculars, a full face helmet, a hat with a brim, a sun visor, or the like. For example, in a case where the information processing device 1 is realized by a pair of binoculars, the various kinds of setting of the pair of binoculars can be customized for an individual on the basis of the personal authentication using the iris. Further, the information processing device 1 may be installed to allow a user to look into like a binocular stereo-microscope, or fixed, for example, by being embedded in the wall.

Next, the configuration of the information processing device 1, which realizes the information processing system according to the present embodiment, will be described with reference to FIG. 4.

2. Configuration

Figure 4:
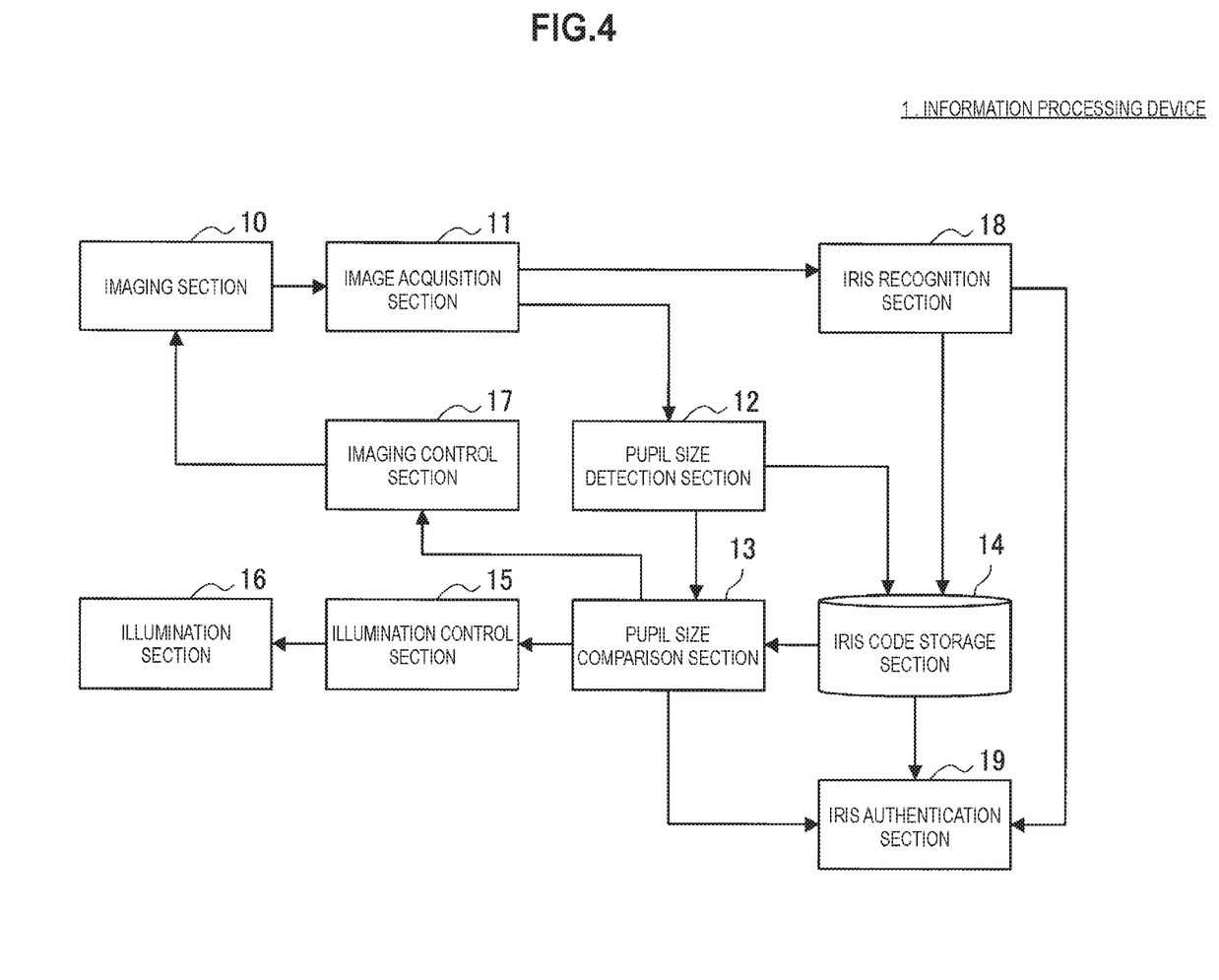
FIG. 4 is a block diagram illustrating an example of a configuration of the information processing device according to the present embodiment.

FIG. 4 is a block diagram illustrating an example of the configuration of the information processing device 1 according to the present embodiment. As illustrated in FIG. 4, the information processing device 1 includes the imaging section 10, an image acquisition section 11, a pupil size detection section 12, a pupil size comparison section 13, an iris code storage section 14, an illumination control section 15, the illumination section 16, an imaging control section 17, an iris recognition section 18, and an iris authentication section 19.

The imaging section 10 is a device that images an eye of a user. For example, in a case where the information processing device 1 is a glasses-type wearable device as illustrated in FIG. 1, the imaging section 10 is inwardly provided to the edge of the lens section to image any one of the left and right eyes of the user when the information processing device 1 is worn by the user.

The image acquisition section 11 acquires an image of the eye imaged by the imaging section 10.

The pupil size detection section 12 detects the pupil size from the image of the eye acquired by the image acquisition section 11. Specifically, for example, the image of the eye is analyzed, the pupil border is decided, and the size thereof (pupil diameter) is detected.

The pupil size comparison section 13 determines whether the pupil size detected by the pupil size detection section 12 is a target pupil size. The target pupil size is a default registration pupil size for iris registration. Further, the target pupil size is a registered pupil size for iris authentication. The registered pupil size is acquired from the iris code storage section 14.

The iris code storage section 14 stores a registered iris code, the pupil size at the time of acquiring the iris code, and a user ID in association with each other.

The illumination control section 15 controls the illumination section 16 on the basis of a result of the comparison made by the pupil size comparison section 13. The illumination section 16 irradiates an eye of the user with light to adjust the size of the pupil. For example, the illumination control section 15 turns on/off the illumination section 16, or adjusts the illuminance (turns up/down the illuminance). As described above, the pupil respectively constricts and dilates as a physiological response when illuminated with increased light and decreased light. Accordingly, in a case where the detected pupil size is greater than the target pupil size, the illumination control section 15 performs control to turn up the illuminance. In a case where the detected pupil size is less than the target pupil size, the illumination control section 15 performs control to turn down the illuminance.

The illumination section 16 is a device that irradiates an eye of a user with visible light. The illumination section 16 is realized, for example, by a light emitting diode (LED). Further, in a case where the information processing device 1 is a glasses-type wearable device as illustrated in FIG. 1, the illumination section 16 is inwardly provided to the edge of the lens section to illuminate any one of the left and right eyes of the user when the information processing device 1 is worn by the user. Further, the illumination section 16 illuminates the other eye different from an eye imaged by the imaging section 10.

The imaging control section 17 controls the imaging of the imaging section 10. For example, in a case where the pupil size detected by the pupil size comparison section 13 does not as agree with the target pupil size, the imaging control section 17 performs control to capture an image again. Further, the imaging control section 17 performs control to capture an image while the illumination control section 15 is irradiating an eye with light.

The iris recognition section 18 recognizes the iris from the image of the eye acquired by the image acquisition section 11. Specifically, the iris recognition section 18 can decide the inner border of the iris (circular border between the iris and the pupil) and the outer border of the iris from the image of the eye, separate the circular iris, extract a feature value by performing polar coordinate conversion on the separated iris image, and generate an iris code through a predetermined encoding process. In a case where the pupil size comparison section 13 determines that the detected pupil size is the target pupil size, the iris recognition section 18 then outputs an iris code generated from the iris image at that time to the iris code storage section 14 at the time of iris registration. Further, in a case where the pupil size comparison section 13 determines that the detected pupil size is the target pupil size, the iris recognition section 18 outputs an iris code generated from the iris image at that time to the iris authentication section 19 at the time of iris authentication.

The iris authentication section 19 compares the iris code output from the iris recognition section 18 with the iris code registered in advance in the iris code storage section 14 to authenticate whether the output iris code and the iris code registered in advance originate from the same individual.

The configuration of the information processing device 1 according to the present embodiment has been described above. The above-described information processing device 1 includes a microcomputer equipped with a central processing unit (CPU), a read only memory (ROM), a random access memory (RAM), and a non-volatile memory. The microcomputer controls each component of the information processing device 1.

Further, the configuration of the information processing device 1 illustrated in FIG. 4 is an example. The present disclosure is not limited thereto. For example, components other than the imaging section 10 and the illumination section 16 may be provided to a separate device (such as a smartphone) from the glasses-type wearable device, and the separate device and the glasses-type wearable device may transmit and receive data through wireless/wired communication, thereby performing illumination control and imaging control, and acquiring a captured image.

3. Operation Processing

Next, the operation processing according to the present embodiment will be described with reference to FIGS. 5 to 6.

<3-1. Registration Process>

Figure 5:
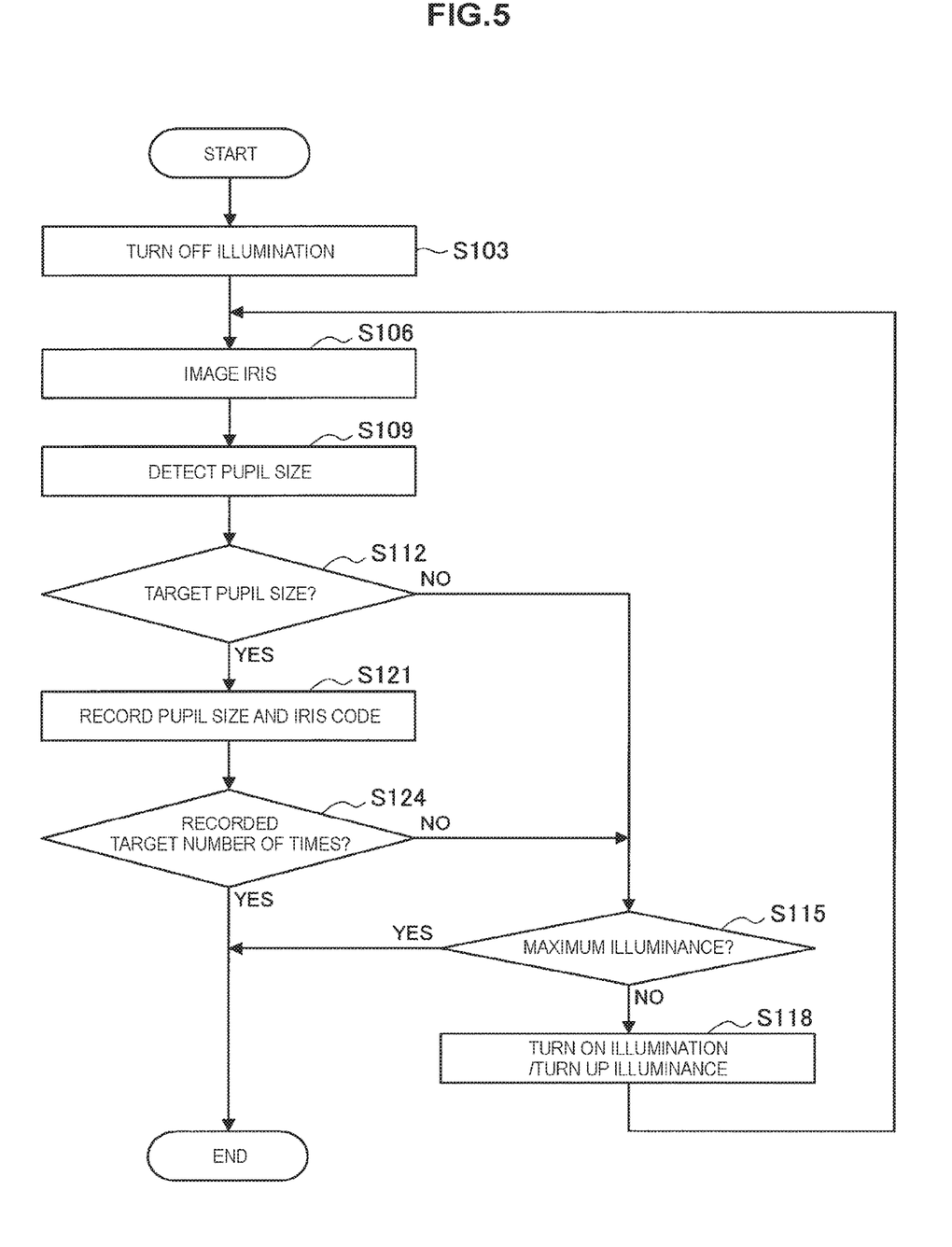
FIG. 5 is a flowchart illustrating an iris code registration process according to the present embodiment.

FIG. 5 is a flowchart illustrating an iris code registration process according to the present embodiment. As illustrated in FIG. 5, in step S103, the illumination control section 15 first performs control to turn off the illumination of the illumination section 16. Additionally, since the pupils of the human eyes constrict faster than dilate, beginning to capture an iris image with the pupils dilated, namely with the illumination off leads to more reduction in the overall imaging time. Accordingly, the registration process begins with the illumination off as an example in the present embodiment.

Next, in step S106, the imaging control section 17 performs control to cause the imaging section 10 to image an iris.

In step S109, the pupil size detection section 12 then detects the pupil size on the basis of the captured image of the iris imaged by the imaging section 10 and acquired by the image acquisition section 11.

Next, in step S112, the pupil size comparison section 13 checks whether the pupil size detected by the pupil size detection section 12 is the target pupil size. Here, the pupil size comparison section 13 checks whether the detected pupil size is a pupil size that is, for example, predefined and appropriate for iris authentication.

Then, in a case where the detected pupil size is not the target pupil size ("No" in S112), the illumination control section 15 determines in step S115 whether the current illuminance is a maximum illuminance.

Next, in a case where the current illuminance is not the maximum illuminance ("No" in S115), the illumination control section 15 performs control to turn on the illumination or turn up the illuminance (increase the intensity of the illumination) in step S118. The maximum illuminance is a preset limit illuminance of the illumination section 16. Further, the limit illuminance of the illumination section 16 is set on the basis of a predetermined standard (value at which the human body is not harmed) with respect to the intensity of light with which the human eyes are irradiated.

It is possible to repeat S103 to S118 described above to adjust the pupil size to the target pupil size. As described above, the pupil respectively constricts and dilates as a physiological response when illuminated with increased light and decreased light. Accordingly, it is possible to adjust the detected pupil size to the target pupil size by gradually turning up the illuminance from the state of off-illumination.

Meanwhile, in a case where the maximum illuminance is reached ("Yes" in S115), the registration process ends.

Next, in a case where the detected pupil size can be adjusted to the target pupil size ("Yes" in S112), the pupil size detected by the pupil size detection section 12 and the iris code recognized and generated by the iris recognition section 18 are stored in the iris code storage section 14 in step S121. At this time, the user ID is also stored. In this way, the iris code is registered.

In step S124, it is then determined whether iris codes are stored (acquired) a target number of times. Storing iris codes based on different pupil sizes makes it possible to improve the accuracy of iris authentication.

In a case where the target number of times is not reached ("No" in S124), the illumination control section 15 then determines whether the current illuminance is the maximum illuminance (S115). If the current illuminance is not the maximum illuminance, the illuminance of the illumination section 16 is turned up (S118), and an iris code is acquired again (S106~S121).

Meanwhile, in a case where the target number of times is reached ("Yes" in S124), the registration process ends.

The iris code registration process according to the present embodiment has been specifically described above. Next, an iris authentication process according to the present embodiment will be described with reference to FIG. 6.

<3-2. Authentication Process>

Figure 6:
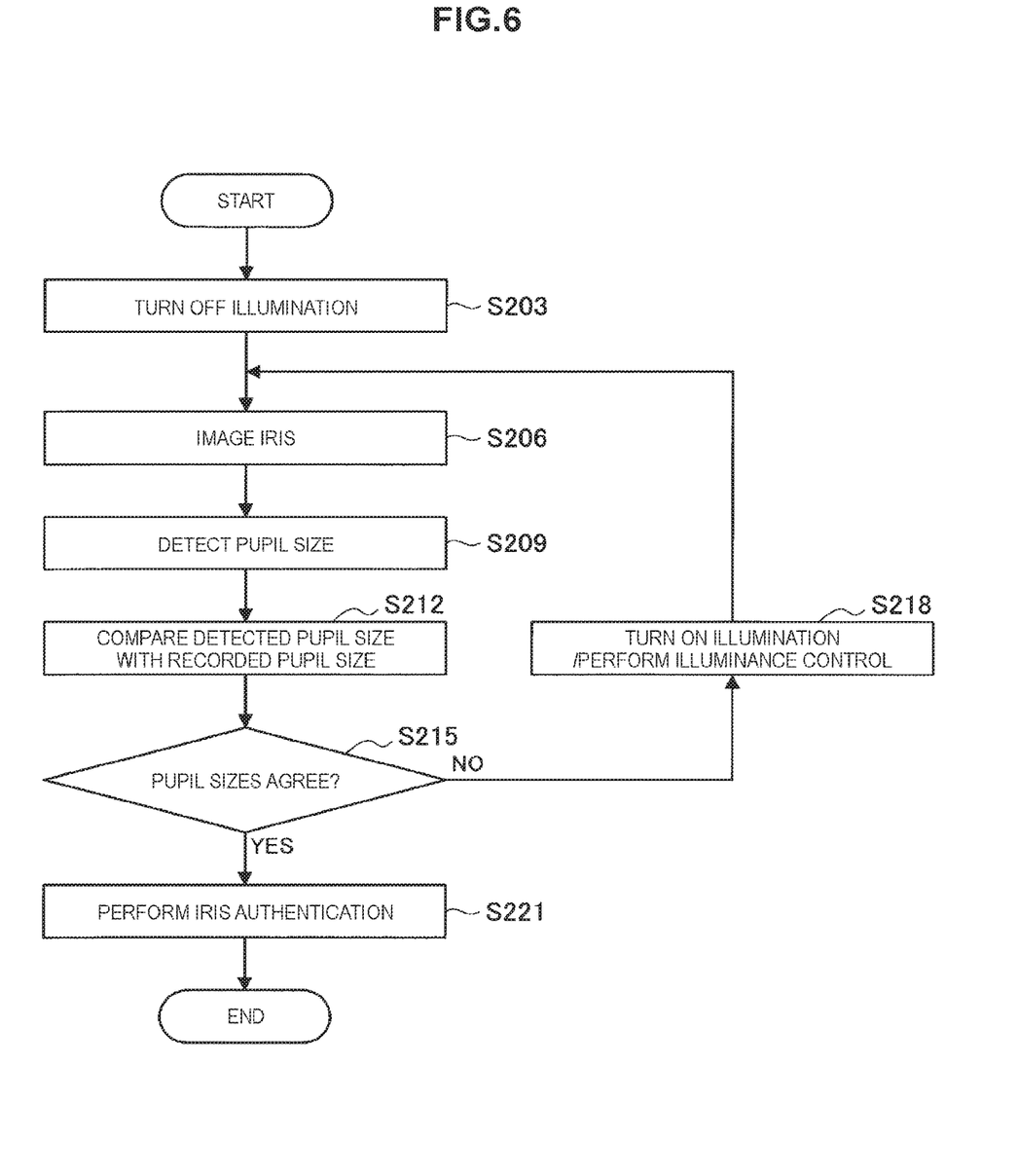
FIG. 6 is a flowchart illustrating an iris authentication process according to the present embodiment.

FIG. 6 is a flowchart illustrating the iris authentication process according to the present embodiment. As illustrated in FIG. 6, in step S203, the illumination control section 15 first performs control to turn off the illumination of the illumination section 16.

Next, in step S206, the imaging control section 17 performs control to cause the imaging section 10 to image an iris.

In step S209, the pupil size detection section 12 then detects the pupil size on the basis of the captured image of the iris imaged by the imaging section 10 and acquired by the image acquisition section 11.

Next, in step S212, the pupil size comparison section 13 compares the pupil size detected by the pupil size detection section 12 with the registered pupil size, and sets a pupil size appropriate for authentication as the target pupil size.

Then, in a case where the pupil size does not agree (the pupil size is different from the target pupil size) ("No" in S215), the illumination control section 15 turns on the illumination or performs illuminance control (turns up/down the illuminance) control in step S218. That is, the illumination control section 15 adjusts the intensity of the illumination to approximate the pupil size to the target pupil size.

Meanwhile, in a case where the pupil size agrees ("Yes" in S215), the iris authentication section 19 performs iris authentication in step S221. That is, the iris authentication section 19 compares the iris code generated by the iris recognition section 18 on the basis of the iris image of the agreeing pupil size with the iris code that is stored in the iris code storage section 14 and has a pupil size which agrees to some extent, and authenticates whether the generated iris code and the stored iris code originate from the same individual.

The iris authentication process according to the present embodiment has been specifically described above. Additionally, in a case where there are registered iris codes corresponding to a single individual, namely an iris code is generated and registered for each of pupil sizes, the iris authentication section 19 may authenticate an iris code for one or each of pupil sizes.

Further, in a case where illuminance control is performed in S218 described above, the illumination section 16 can adjust not only the magnitude of the intensity of the illumination, but also the amount of light with which an eye is irradiated, by controlling, in a case where a lens section of the glasses-type wearable device includes a light-blocking filter, the light-blocking filter.

Further, in a case where the illumination sections 16 are provided, the illumination control section 15 can adjust the overall illuminance on the basis of the number of illumination sections 16 that are turned on and the intensity of the illumination of each illumination section 16.

Further, the imaging control section 17 may also perform control to capture an image in cooperation with the illumination control section 15. For example, when the illumination section 16 performs illumination, the imaging control section 17 captures an image a predetermined time after the start of the illumination. This is because, in a case where the human eye is irradiated with light, the light reflex that the pupil of the eye varies and the consensual light reflex (the pupil that is not irradiated with light similarly varies) take the predetermined time.

4. Supplemental Information

Next, the information processing system according to the present embodiment will be supplementarily described. The information processing device 1 described with reference to FIG. 1 includes the illumination section 16 and the imaging section 10 that are disposed to irradiate any one of the left and right eyes with light, and to image the other eye. The present disclosure is not, however, limited thereto.

Figure 7:
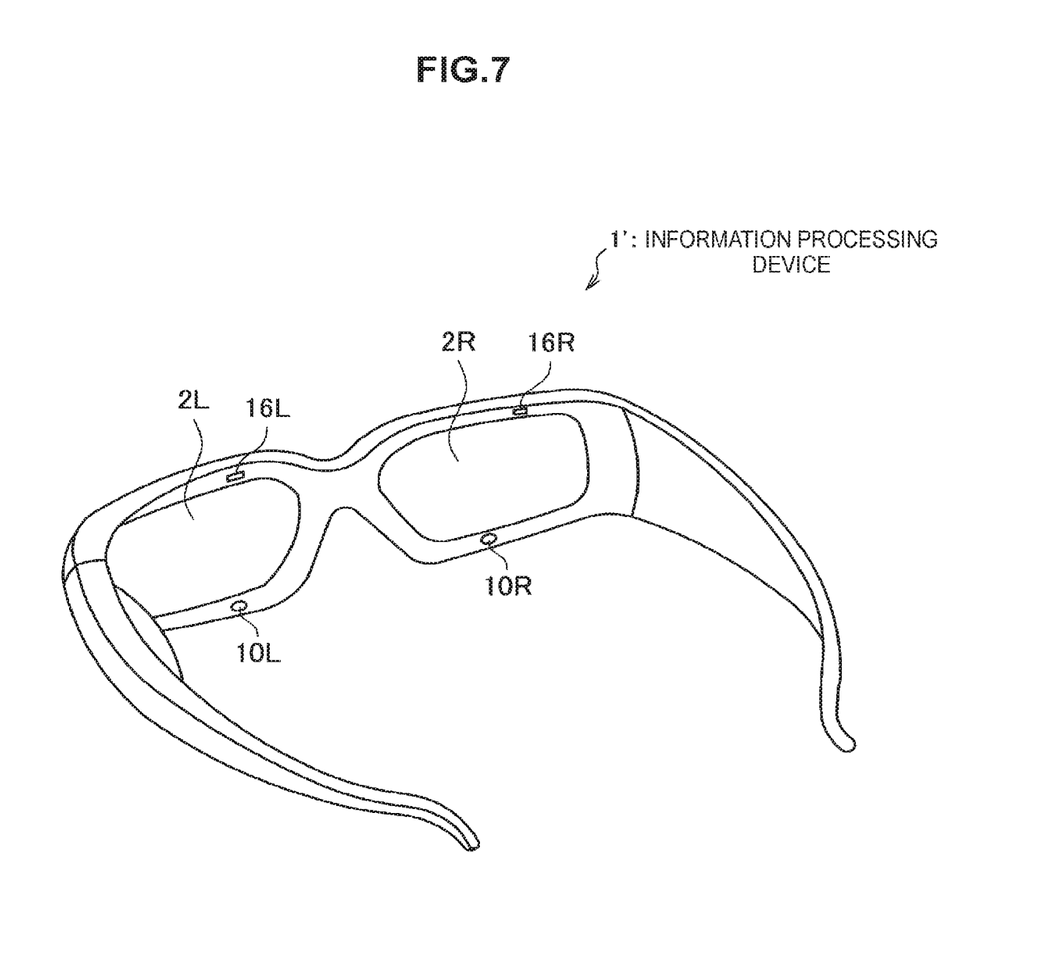
FIG. 7 is a diagram that describes an information processing device according to a modification of the present embodiment.

FIG. 7 is a diagram that describes an information processing device 1' according to a modification of the present embodiment. As illustrated in FIG. 7, the information processing device 1' is realized by a glasses-type wearable device similarly to the information processing device 1 illustrated in FIG. 1, and includes the right-eye lens section 2R and the left-eye lens section 2L that are respectively positioned in front of the right eye of a user and the left eye of the user when worn by the user. Illumination sections 16R and 16L are respectively provided to the edge of the right-eye lens section 2R and the edge of the left-eye lens section 2L in the present modification. Further, imaging sections 10R and 10L are respectively provided to the edge of the right-eye lens section 2R and the edge of the left-eye lens section 2L.

Such a structure allows the information processing device 1' to acquire a clear iris image of any of the right eye and the left eye. That is, in a case where an iris image of the right eye is acquired, the information processing device 1' has the illumination section 16L on the edge of the left-eye lens section 2L irradiate the left eye, and has the imaging section 10R on the edge of the right-eye lens section 2R image the right eye. Further, in a case where an iris image of the left eye is acquired, the information processing device 1' has the illumination section 16R on the edge of the right-eye lens section 2R irradiate the right eye, and has the imaging section 10L on the edge of the left-eye lens section 2L image the left eye. In a case where an iris image of one of the left and right eyes is acquired, this makes it possible to acquire a clear iris image having no reflected light (bright spots) by irradiating the other eye and imaging the eye that is not irradiated.

Since the human left and right eyes have different irises, a right-eye iris code and a left-eye iris code are respectively necessary in a case where the registered iris code is for a right eye and the registered iris code is for a left eye. Accordingly, if it is possible to acquire clear iris images of both of the left and right eyes, the convenience will be improved. Further, the information processing device 1' allows the iris codes of both eyes to be registered and authenticated.

5. Conclusion

As described above, the information processing system according to the embodiment of the present disclosure can capture a clear iris image having no reflected light of illumination without interfering with a user's field of view. This makes it possible to eliminate the necessity to capture an iris image again at the time of iris code registration because of an unclear iris image, and further improve the accuracy of authentication at the time of authentication.

Further, it is possible to miniaturize the device.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the information processing device 1 illustrated in FIG. 1 includes the imaging section 10 and the illumination section 16 that are integrated with each other. The imaging section 10 and the illumination section 16 may also be, however, provided to separate devices. For example, the information processing system may be a system in which the imaging section 10 is provided to a monocular wearable device, and the illumination section 16 is provided to an installed/fixed device. In this case, the illumination section 16 irradiates one of the eyes of a user with light from a super-directive spot light, and the other eye is imaged by the imaging section 10 of the monocular wearable device. Further, the information processing system may be a system in which the imaging section 10 and the illumination section 16 are separately provided to wearable devices (such as a SmartBand, a SmartWatch, or a SmartEyeglass), smartphones, or the like worn by a user.

Further, the imaging sections 10L and 10R, and the illumination section 16L and 16R of the information processing device 1' illustrated in FIG. 7 are provided to the same device. The imaging section 10L and the illumination section 16L, and the imaging section 10R and the illumination section 16R may also be provided to separate devices.

It is also possible to create a computer program for causing hardware such as a CPU, a ROM, and a RAM built in the above-described information processing devices 1 and 1' to perform the functions of the information processing devices 1 and 1'. Further, there is also provided a computer-readable storage medium having the computer program stored therein.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control system including:

an illumination section configured to irradiate any one of left and right eyes with light;

an imaging section configured to image the other eye different from the one of the left and right eyes; and a control section configured to perform control to cause the imaging section to image the other eye while the illumination section is irradiating the one of the left and right eyes with light.

(2)

The control system according to (1), further including:

an iris recognition section configured to recognize an iris image from a captured image by the imaging section.

(3)

The control system according to (2), further including:

a pupil size detection section configured to detect a size of a pupil recognized from the captured image, wherein the control section performs illumination control to acquire a target pupil size in accordance with the detected pupil size.

(4)

The control system according to (3), wherein in a case where the detected pupil size is greater than the target pupil size, the control section performs illumination control to turn up an illuminance.

(5)

The control system according to (3), wherein in a case where the detected pupil size is less than the target pupil size, the control section performs illumination control to turn down an illuminance.

(6)

The control system according to any one of (2) to (5), wherein the control section performs control to store an iris code based on the recognized iris image, a pupil size at time of recognizing the iris image, and a user ID in association with each other.

(7)

The control system according to any one of (2) to (6), further including:

an iris authentication section configured to perform iris authentication on the basis of the recognized iris image.

(8)

The control system according to any one of (1) to (7), wherein the control section performs control to begin to capture an image with illumination of the illumination section off.

(9)

An information processing device including:

an imaging section configured to image any one of left and right eyes;

an illumination section configured to irradiate the other eye different from the one of the left and right eyes with light; and a control section configured to perform control to cause the imaging section to image the one of the left and right eyes while the illumination section is irradiating the other eye with light.

(10)

A control method including:

performing control to cause, while an illumination section is irradiating any one of left and right eyes with light, an imaging section to image the other eye different from the one of the left and right eyes.

(11)

A program for causing a computer to function as:

a control section configured to perform control to cause, while an illumination section is irradiating any one of left and right eyes with light, an imaging section to image the other eye different from the one of the left and right eyes.

REFERENCE SIGNS LIST 1 information processing device
10 imaging section
11 image acquisition section
12 pupil size detection section
13 iris size comparison section
14 iris code storage section
15 illumination control section
16 illumination section
17 imaging control section
18 iris recognition section
19 iris authentication section
2R right-eye lens section
2L left-eye lens section
3R right eye
3L left eye
30 iris
31 pupil
33 bright spot
40, 41 captured image
100 imaging section
160 illumination section

The invention claimed is:

1. A control system comprising:
circuitry configured to:
irradiate one of left and right eyes with light from a light source included in eyeglasses;
image the other eye different from the one of the left and right eyes;
perform control to cause the imaging of the other eye during the irradiation of the one of the left and right eyes with the light;
compare a pupil size in a captured image to a target pupil size;
increase a light amount of the light source included in the eyeglasses if the pupil size is greater than the target pupil size; and
decrease the light amount of the light source included in the eyeglasses if the pupil size is smaller than the target pupil size.

2. The control system according to claim 1, wherein the circuitry is further configured to recognize an iris image from a captured image.

3. The control system according to claim 2, Wherein the circuitry is further configured to
detect a size of a pupil recognized from the captured image, and
perform illumination control to acquire a target pupil size in accordance with the detected pupil size.

4. The control system according to claim 3, wherein in a case where the detected pupil size is greater than the target pupil size, the circuitry performs illumination control to turn up an illuminance.

5. The control system according to claim 3, wherein in a case where the detected pupil size is less than the target pupil size, the circuitry performs illumination control to turn down an illuminance.

6. The control system according to claim 2, wherein the circuitry performs control to store an iris code based on the recognized iris image, a pupil size at time of recognizing the iris image, and a user ID in association with each other.

7. The control system according to claim 2, wherein the circuitry is further configured to perform iris authentication on the basis of the recognized iris image.

8. The control system according to claim 1, wherein the circuitry performs control to begin to capture an image before irradiation with the light begins.

9. The control system according to claim 1, wherein the circuitry images the other eye from a rim of the eyeglasses.

10. The control system according to claim 1, wherein the circuitry is further configured to image the other eye without interfering with a field of view of the other eye.

11. A control method comprising:
performing control to irradiate one of left and right eyes with light from a light source included in eyeglasses;
performing control to image the other eye different from the one of the left and right eyes;
performing control to cause the imaging of the other eye during the irradiation of the one of the left and right eyes with the light;
performing control to compare a pupil size in a captured image to a target pupil size;
performing control to increase a light amount of the light source included in the eyeglasses if the pupil size is greater than the target pupil size; and
performing control to decrease the light amount of the light source included in the eyeglasses if the pupil size is smaller than the target pupil size.

12. The control method according to claim 11, further comprising:
    performing the control to cause the imaging of the other eye without interfering with a field of view of the other eye.

13. A non-transitory computer-readable medium encoded with computer-readable instructions that, when executed by processing circuitry, cause the processing circuitry to perform a control method comprising:
    performing control to irradiate one of left and right eyes with light from a light source included in eyeglasses;
    performing control to image the other eye different from the one of the left and right eyes;
    performing control to cause the imaging of the other eye during the irradiation of the one of the left and right eyes with the light;
    performing control to compare a pupil size in a captured image to a target pupil size;
    performing control to increase a light amount of the light source included in the eyeglasses if the pupil size is greater than the target pupil size; and
    performing control to decrease the light amount of the light source included in the eyeglasses if the pupil size is smaller than the target pupil size.

14. The non-transitory computer-readable medium according to claim 13, further causing the processing circuitry to perform the control to cause the imaging of the other eye without interfering with a field of view of the other eye.

* * * * *